(12) United States Patent
Harper, II (10) Patent No.: US 9,891,090 B1
(45) Date of Patent: Feb. 13, 2018

(54) MEASURING CUP WITH CAP, GRIP, AND LEVELER

(71) Applicant: John L. Harper, II, Coopersburg, PA (US)

(72) Inventor: John L. Harper, II, Coopersburg, PA (US)

( * ) Notice: Subject to any disclaimer, the term of this patent is extended or adjusted under 35 U.S.C. 154(b) by 0 days.

(21) Appl. No.: 15/620,995

(22) Filed: Jun. 13, 2017

(51) Int. Cl.
G01F 19/00 (2006.01)

(52) U.S. Cl.
CPC .................... G01F 19/00 (2013.01)

(58) Field of Classification Search
CPC ............................. G01F 19/002; G01F 19/00
USPC ........................................................ 73/427
See application file for complete search history.

(56) References Cited

U.S. PATENT DOCUMENTS

| 841,310 A | 1/1907 | Carlson | |
|---|---|---|---|
| 2,158,704 A | 5/1939 | Ligon | |
| 3,049,926 A * | 8/1962 | Victor | G01F 19/002 30/326 |
| 3,415,376 A | 12/1968 | Smith | |
| D266,819 S | 11/1982 | Doyel | |
| 5,662,249 A | 9/1997 | Grosse | |
| 7,980,131 B2 | 7/2011 | Barton | |
| 2005/0017028 A1* | 1/2005 | Rea | G01F 19/002 222/460 |
| 2014/0144926 A1 | 5/2014 | Wolf | |

FOREIGN PATENT DOCUMENTS

JP          08282715 A   * 10/1996   ........... B65D 51/246

* cited by examiner

*Primary Examiner* — Lisa Caputo
*Assistant Examiner* — Jamel Williams
(74) *Attorney, Agent, or Firm* — Kyle A. Fletcher, Esq.

(57) ABSTRACT

The measuring cup is a calibrated measuring device that configured for use in measuring volume. The measuring cup is configured for use with an analyte material selected from the group consisting of: a fluid analyte material, a semi-rigid analyte material, a granular analyte material, or a crystalline analyte material. The measuring cup comprises a cap, a body, and a leveler. The cap and the leveler are attached to the body. The body is a contained and calibrated volume that is used to measure the volume of the analyte material. The cap is a handle that is used to manipulate the measuring cup. The leveler is a device that levels the analyte material within the body of the measuring cup.

18 Claims, 4 Drawing Sheets

MEASURING CUP WITH CAP, GRIP, AND LEVELER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of instruments including the measurement of volume, more specifically, a calibrated volume measurement device.

SUMMARY OF INVENTION

The measuring cup is a calibrated measuring device that is configured for use in measuring volume. The measuring cup is configured for use with an analyte material selected from the group consisting of: a fluid analyte material, a semi-rigid analyte material, a granular analyte material, or a crystalline analyte material. Examples of a fluid analyte material suitable for use with the measuring cup include, but are not limited to, a water or a fat in a fluid phase. An example of a semi-rigid analyte material suitable for use with the measuring cup includes, but is not limited to, a vegetable shortening. Examples of a granular analyte material suitable for use with the measuring cup includes, but is not limited to, rice or flour. An example of a crystalline analyte material suitable for use with the measuring cup includes, but is not limited to, sugar. The measuring cup comprises a cap, a body, and a leveler. The cap and the leveler are attached to the body. The body is a contained and calibrated volume that is to used measure the volume of the analyte material. The cap is a handle that is used to manipulate the measuring cup. The leveler is a device that levels the analyte material within the body of the measuring cup.

These together with additional objects, features and advantages of the measuring cup will be readily apparent to those of ordinary skill in the art upon reading the following detailed description of the presently preferred, but nonetheless illustrative, embodiments when taken in conjunction with the accompanying drawings.

In this respect, before explaining the current embodiments of the measuring cup in detail, it is to be understood that the measuring cup is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the measuring cup.

It is therefore important that the claims be regarded as including such equivalent construction insofar as they do not depart from the spirit and scope of the measuring cup. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
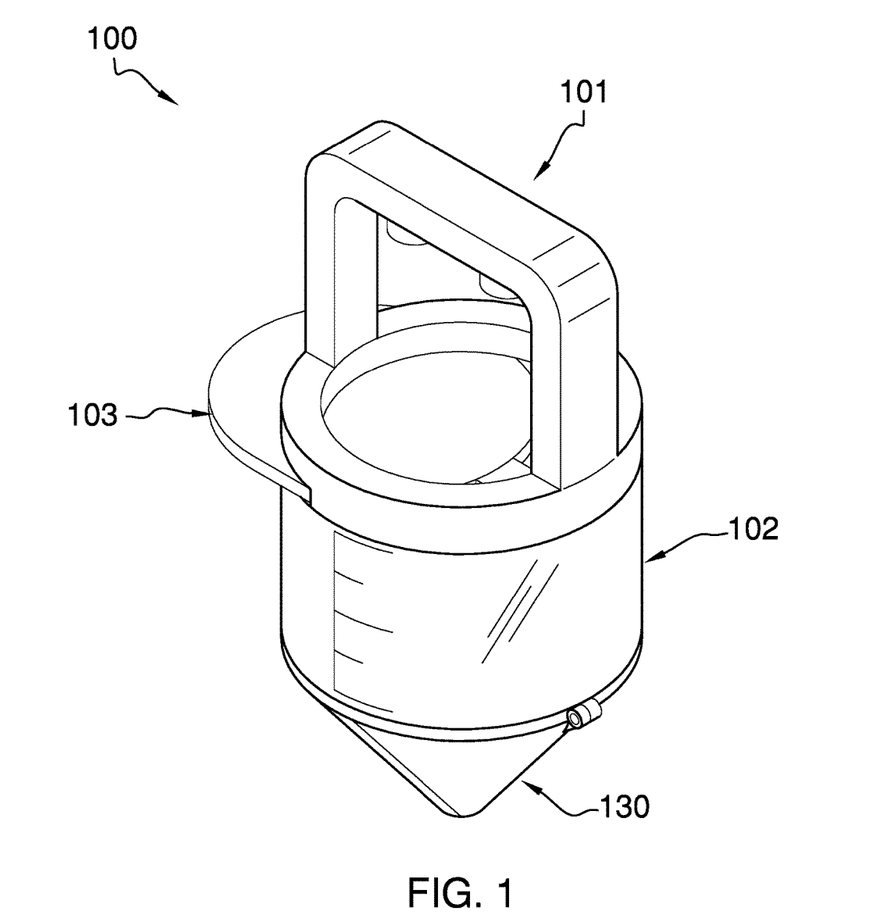
FIG. 1 is a perspective view of an embodiment of the disclosure.
Figure 2:
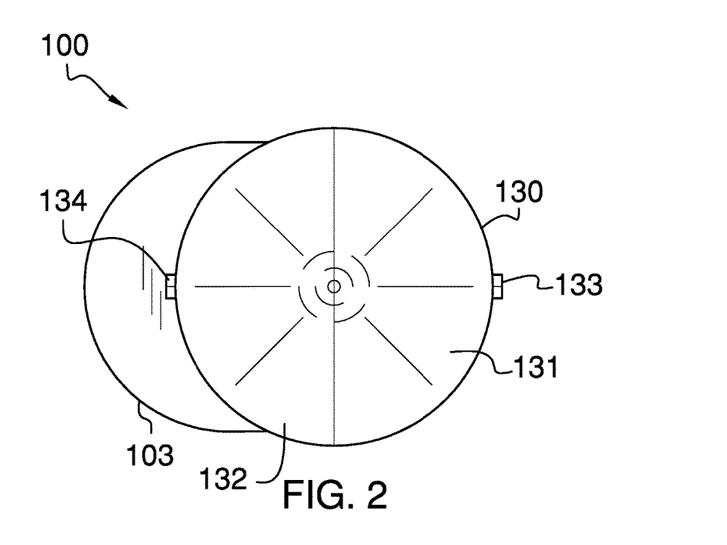
FIG. 2 is a bottom view of an embodiment of the disclosure.
Figure 3:
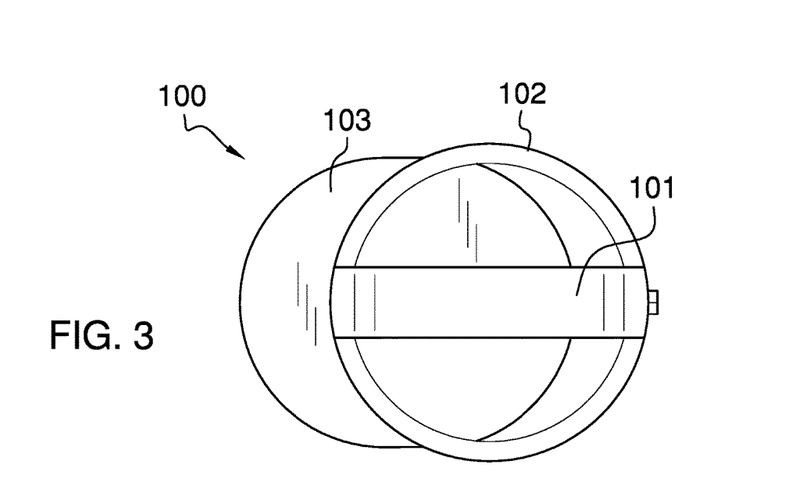
FIG. 3 is a top view of an embodiment of the disclosure.
Figure 4:
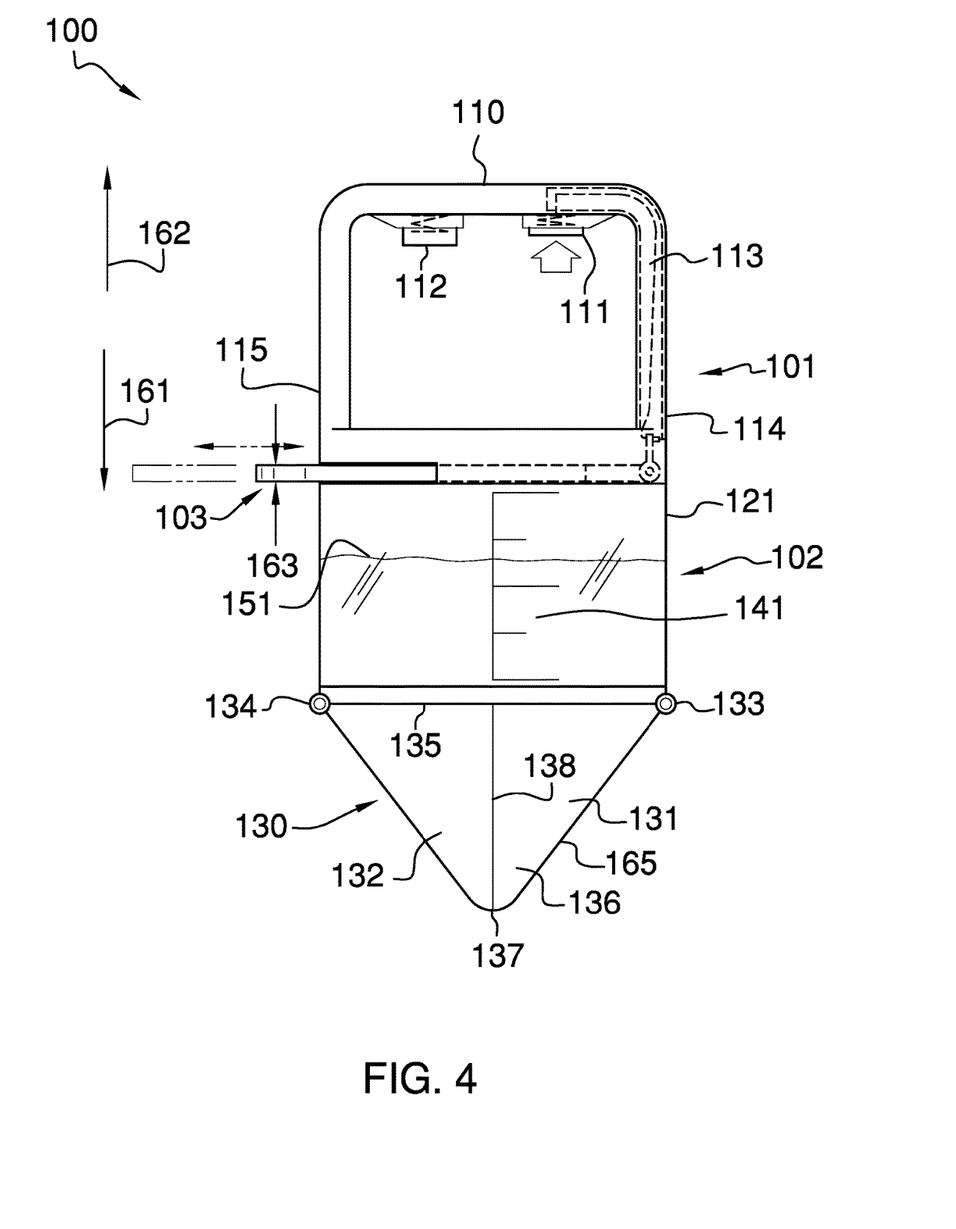
FIG. 4 is a front view of an embodiment of the disclosure.
Figure 5:
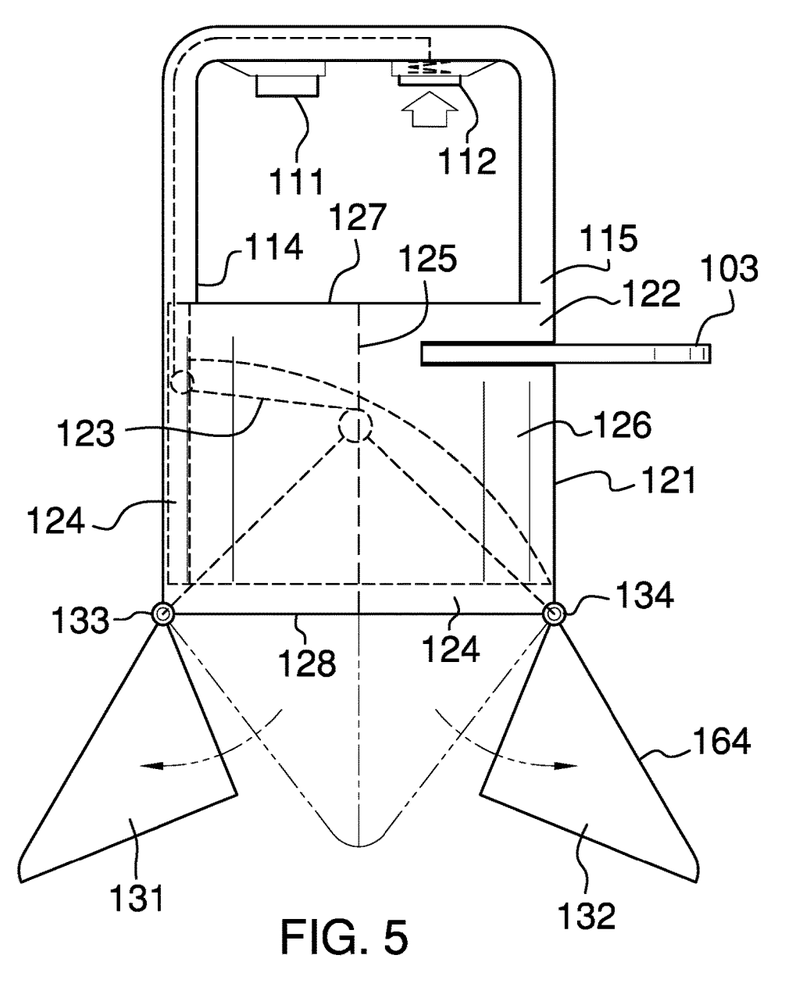
FIG. 5 is a rear view of an embodiment of the disclosure.

Detailed reference will now be made to one or more potential embodiments of the disclosure, which are illustrated in FIGS. 1 through 5.

The measuring cup 100 (hereinafter invention) is a calibrated measuring device that configured for use in measuring volume. The invention 100 is configured for use with an analyte material 151. The analyte material 151 refers to the material being measured within the invention 100. The invention 100 is selected from the group consisting of: a fluid analyte material 151, a semi-rigid analyte material 151, a granular analyte material 151, or a crystalline analyte material 151. Examples of a fluid analyte material 151 suitable for use with the invention 100 include, but are not limited to, a water or a fat in a fluid phase. An example of a semi-rigid analyte material 151 suitable for use with the invention 100 includes, but is not limited to, a vegetable shortening.

Examples of a granular analyte material 151 suitable for use with the invention 100 includes, but is not limited to, rice or flour. An example of a crystalline analyte material 151 suitable for use with the invention 100 includes, but is not limited to, sugar. The invention 100 comprises a cap 101, a body 102, and a leveler 103. The cap 101 and the leveler 103 are attached to the body 102. The body 102 is a contained and calibrated volume that is used to measure the volume of the analyte material 151. The cap 101 is a handle that is used to manipulate the invention 100. The leveler 103 is a device that levels the analyte material 151 within the body 102 of the invention 100.

The cap 101 is a structure that forms the superior 162 end of the invention 100. The cap 101 is a handle that is used to manipulate the invention 100. The cap 101 comprises a grip 110, a first lever 111, and a second lever 112. The grip 110 is further defined with a first end 114 and a second end 115.

The grip 110 is a hollow tubular structure that allows the invention 100 to be grasped by a hand. The grip 110 is formed with all apertures and form factors necessary to allow the grip 110 to accommodate the use of the first lever 111 and the second lever 112 in the operation of the invention 100. The grip 110 is a U shaped structure that attaches to the superior 162 end of the body 102. The grip 110 comprises a center chamber 113.

The first lever 111 is a mechanical trigger that is used to open the body 102 to release the measured analyte material 151 from the body 102. The second lever 112 is a mechanical trigger that is used to operate the leveler 103. The center chamber 113 is a negative space that forms a continuous channel from the first end 114 of the grip 110 to the second end 115 of the grip 110.

The first end 114 of the grip 110 attaches to the superior 162 cylinder end 127 such that the center chamber 113 is aligned with the coaxial chamber 124 of the cylinder 121. The alignment of the center chamber 113 and the coaxial chamber 124 allows an object to pass from the center chamber 113 into the coaxial chamber 124. The second end 115 of the grip 110 attaches to the superior 162 cylinder end 127. The superior 162 cylinder end 127 is discussed in greater detail elsewhere in this disclosure.

The body 102 is a multifaceted structure that forms a contained volume within which the analyte material 151 is placed for volume measurement. The body 102 comprises a cylinder 121 and a cone 130. The cylinder 121 is further defined with a cylinder center axis 125, a cylinder face 126, a superior 162 cylinder end 127, and an inferior 161 cylinder end 128. The cone 130 is further defined with a cone base 135, a cone face 136, and a cone apex 137.

The body 102 further comprises a calibrating indicia 141. The calibrating indicia 141 refers to a plurality of markings that are formed on the body 102 (including both the cylinder face 126 and the cone face 136). Each calibrating indicia 141 indicates a level that is associated with a volume of analyte material 151 that is contained within the body 102. The level indicated by each calibrating indicia 141 communicates the volume within the body 102 from the cone apex 137 to a hypothetical plane that: 1) contains a calibrating indicia 141 and that is perpendicular to the cone center axis 138 of the cone 130.

The cylinder 121 is a hollow cylindrical structure formed from a transparent material. The interior volume of the cylinder 121 forms the bulk of the calibrated containment of the invention 100. The cylinder 121 comprises a leveler slot 122, a linkage 123, and a coaxial chamber 124.

The linkage 123 is a spring driven mechanical device that mechanically connects the first lever 111 to the first hinge 133 and to the second hinge 134. The linkage 123 allows the first lever 111 to release the first hinge 133 and to release the second hinge 134 to release the analyte material 151. The first hinge 133 and the second hinge 134 are discussed in greater detail elsewhere in this disclosure.

The coaxial chamber 124 is a negative space that is formed within the curved plate that forms the cylinder 121. The coaxial chamber 124 is formed from a segment of a cylindrical space that is positioned in a coaxial manner around the cylinder center axis 125 of the cylinder 121.

The cylinder center axis 125 refers to the center axis of the geometric cylindrical structure that forms the cylinder 121. The cylinder face 126 refers to the face of the geometric cylindrical structure that forms the cylinder 121. The superior 162 cylinder end 127 refers to the base of the geometric cylindrical structure that forms the cylinder 121 that is proximal to the superior 162 side of the invention 100. The inferior 161 cylinder end 128 refers to the base of the geometric cylindrical structure that forms the cylinder 121 that is proximal to the inferior 161 side of the invention 100.

The leveler 103 is an oval shaped plate that is used to level the analyte material 151 within the body 102. The leveler 103 is further defined with a thickness 163. The leveler 103 is further defined with a major axis and a minor axis. The minor axis of the leveler 103 is lesser than the diameter of the cylinder 121 such that the leveler 103 can be inserted through the leveler slot 122 into the interior of the cylinder 121. The leveler 103 is inserted into the interior of the cylinder 121 to "level" the superior 162 surfaces of the analyte material 151 such that an accurate volume reading may be made. The leveler 103 is installed with a pivot which allows the leveler 103 to "sweep" over the analyte material 151. The leveler 103 is mechanically linked with the second lever 112 such that the triggering of the second lever 112 mechanically operates the leveler 103. Methods to use a lever to rotate an object around a pivot are well known and documented in the mechanical arts.

The leveler slot 122 is a slot shaped aperture that is formed through the cylinder face 126 of the cylinder 121. The inner dimension of the leveler slot 122 is greater than the thickness 163 of the outer dimension of the leveler 103 such that the leveler 103 can be inserted into the interior space of the cylinder 121 through the leveler slot 122.

The cone 130 is a hollow cone shaped structure formed from a transparent material. In the first potential embodiment of the disclosure, the cone apex 137 is rounded to allow for easy cleaning of the invention 100. The cone 130 is divided into two partial cone structures by a plane that is parallel to the cone center axis 138. In the first potential embodiment of the disclosure, the plane that divides the cone 130 contains the cone center axis 138 such that the two partial cone structures are identical. The cone 130 comprises a first bifurcation 131, a second bifurcation 132, a first hinge 133, and a second hinge 134.

The first bifurcation 131 is a first partial cone structure selected from the two partial cone structures. The second bifurcation 132 is a second partial cone structure selected from the two partial cone structures. The first bifurcation 131 are rejoined along the second bifurcation 132 are rejoined along the line of bifurcation, the cone 130 is effectively reassembled.

In the first potential embodiment of the disclosure, the first bifurcation 131 and the second bifurcation 132 are identical. The first bifurcation 131 and the second bifurcation 132 are joined together to form the cone 130. When the cone 130 is formed the cone 130 is said to be in the closed position 165. When the first bifurcation 131 and the second bifurcation 132 are separated, the cone 130 is said to be in the open position 164. When the cone 130 is in the open position 164, the analyte material 151 will fall out of the body 102.

The first hinge 133 is a readily and commercially available spring loaded hinge that attaches the first bifurcation 131 to the inferior 161 cylinder end 128 of the cylinder 121. The second hinge 134 is a readily and commercially available spring loaded hinge that attaches the second bifurcation 132 to the inferior 161 cylinder end 128 of the cylinder 121. The first hinge 133 and the second hinge 134 are identical. The first hinge 133 attaches the first bifurcation 131 to the cylinder 121 such that when the cone 130 is in the open position 164 the spring of the first hinge 133 in in its relaxed shape. The second hinge 134 attaches the second bifurcation 132 to the cylinder 121 such that when the cone 130 is in the open position 164 the spring of the second hinge 134 in in its relaxed shape.

The spring of the first hinge 133 is held in the closed position 165 using a first detent that connects through the linkage 123 to the first lever 111 such that the first lever 111 will release the first detent holding the first hinge 133 in the closed position 165. The second hinge 134 is held in the closed position 165 using a second detent that connects through the linkage 123 to the first lever 111 such that the first lever 111 will release the second detent holding the second hinge 134 in the closed position 165.

The cone base 135 refers to the base of the geometric cone structure that forms the cone 130. The diameter of the cone base 135 equals the diameter of the inferior 161 cylinder end 128 such that the cone base 135 can be aligned and attached to the inferior 161 cylinder end 128. The cone face 136 refers to the face of the geometric cone structure that forms the cone 130. The cone apex 137 refers to the apex of the geometric cone structure that forms the cone 130. In the first potential embodiment of the disclosure, the cone apex 137 is rounded. The cone center axis 138 refers to the center axis of the geometric cone structure that forms the cone 130.

To use the invention 100, the first bifurcation 131 and the second bifurcation 132 are manually held in the closed position 165 while the first hinge 133 and the second hinge 134 and placed in their closed and locked positions. The analyte material 151 is placed in the body 102 and measured using the calibrating indicia 141. Once the analyte material 151 has been appropriately measured, the first lever 111 is activated to release the first hinge 133 and the second hinge 134 thereby opening the body 102 to release the analyte material 151. Methods to form a linkage 123 as described in this disclosure are well known and documented in the mechanical arts.

The following definitions were used in this disclosure:

Align: As used in this disclosure, align refers to an arrangement of objects that are: 1) arranged in a straight line; or, 2) arranged to give a directional sense of a plurality of parallel lines.

Cavity: As used in this disclosure, a cavity is an empty space or negative space that is formed within an object.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or cone like structure. When the center axes of two cylinder or like structures share the same line they are said to be aligned. When the center axes of two cylinder like structures do not share the same line they are said to be offset.

Channel: As used in this disclosure, a channel is a tubular passage through which an object or fluid is passed through.

Coaxial: As used in this disclosure, coaxial is an term that refers to a first object that is inserted or contained within a second object such: 1) that the first object and the second object share the same center point if the or first object and the second object are treated as a two dimensional objects; or, 2) that the first object and the second object share the same center axis if the or first object and the second object are treated as three dimensional objects.

Concave: As used in this disclosure, concave is used to describe: 1) a surface that resembles the interior surface of a sphere; or, 2) a function with a curvature structure wherein a chord that connects any two points of the function will be lesser than (graphically below) or equal to the value of the function at any point along the chord.

Cone: As used in this disclosure, a cone is a surface that is generated by rotating a triangle around one of the legs of the triangle. If a line that is perpendicular to the base that is drawn from the center of the base goes through the vertex of the triangle then the cone is called a right cone. A cone is a type of quadric surface. The cone is a pyramid with a circular base.

Cylinder: As used in this disclosure, a cylinder is a geometric structure defined by two identical flat and parallel ends, also commonly referred to as bases, which are circular in shape and connected with a single curved surface, referred to in this disclosure as the face. The cross section of the cylinder remains the same from one end to another. The axis of the cylinder is formed by the straight line that connects the center of each of the two identical flat and parallel ends of the cylinder. Unless otherwise stated within this disclosure, the term cylinder specifically means a right cylinder which is defined as a cylinder wherein the curved surface perpendicularly intersects with the two identical flat and parallel ends.

Detent: As used in this disclosure, a detent is a device for positioning and holding one mechanical part in relation to another in a manner such that the device can be released by force applied to one or more of the parts.

Diameter: As used in this disclosure, a diameter of an object is a straight line segment that passes through the center of an object. The line segment of the diameter is terminated at the perimeter or boundary of the object through which the line segment of the diameter runs.

Exterior: As used in this disclosure, the exterior is use as a relational term that implies that an object is not contained within the boundary of a structure or a space.

Form Factor: As used in this disclosure, the term form factor refers to the size and shape of an object.

Fulcrum: As used in this disclosure, a fulcrum is a support around which a lever rotates.

Grip: As used in this disclosure, a grip is an accommodation formed within an object that allows the object to be grasped by a hand.

Handle: As used in this disclosure, a handle is an object by which a tool, object, or door is held or manipulated with the hand.

Hinge: As used in this disclosure, a hinge is a device that permits the turning, rotating, or pivoting of a first object relative to a second object.

Housing: As used in this disclosure, a housing is a rigid casing that encloses and protects one or more devices.

Indicia: As used in this disclosure, the term indicia refers to a set of markings that identifies a sentiment.

Inferior: As used in this disclosure, the term inferior refers to a directional reference that is parallel to and in the same direction as the force of gravity.

Inner Dimension: As used in this disclosure, the term inner dimension describes the span from a first inside or interior surface of a container to a second inside or interior surface of a container. The term is used in much the same way that a plumber would refer to the inner diameter of a pipe.

Interior: As used in this disclosure, the interior is use as a relational term that implies that an object is contained within the boundary of a structure or a space.

Lever: As used in this disclosure, is a shaft that rotates around a pivot point commonly referred to as a shaft.

Major and Minor Axes: As used in this disclosure, the major axis axes refer to a pair of perpendicular axis that are defined within a structure. The length of the major axis is always greater than or equal to the length of the minor axis.

Negative Space: As used in this disclosure, negative space is a method of defining an object through the use of open or empty space as the definition of the object itself, or, through the use of open or empty space to describe the boundaries of an object.

Outer Dimension: As used in this disclosure, the term outer dimension describes the span from a first exterior or outer surface of a tube or container to a second exterior or outer surface of a tube or container. The term is used in much the same way that a plumber would refer to the outer diameter of a pipe.

Oval: As used in this disclosure, an oval is a geometric shape that is formed in the shape of a "squished" circle similar in form to an ellipse. The difference between an oval and an ellipse is that an ellipse can be described by a mathematical formula while an oval has no such description.

Perimeter: As used in this disclosure, a perimeter is one or more curved or straight lines that bounds an enclosed area on a plane or surface. The perimeter of a circle is commonly referred to as a circumference.

Relaxed Shape: As used in this disclosure, a structure is considered to be in its relaxed state when no shear, strain, or torsional forces are being applied to the structure.

Rounded: A used in this disclosure, the term rounded refers to the replacement of an apex or vertex of a structure with a (generally smooth) curvature wherein the concave portion of the curvature faces the center of the structure.

Semi-Rigid Structure: As used in this disclosure, a semi-rigid structure is a solid structure that is stiff but not wholly inflexible and that will deform under force before breaking. A semi-rigid structure may or may not behave in an elastic fashion in that a semi-rigid structure need not return to a relaxed shape.

Sentiment: As used in this disclosure, a sentiment refers to a symbolic meaning or message that is communicated through the use of an image, potentially including a text based image.

Slot: As used in this disclosure, a slot is a long narrow groove or aperture that is formed in an object.

Spring: As used in this disclosure, a spring is a device that is used to store mechanical energy. This mechanical energy will often be stored by: 1) deforming an elastomeric material that is used to make the device; 2) the application of a torque to a rigid structure; or 3) a combination of the previous two items.

Superior: As used in this disclosure, the term superior refers to a directional reference that is parallel to and in the opposite direction of the force of gravity.

Torsion Spring: As used in this disclosure, a torsion spring is a mechanical device that stores mechanical energy through an opposing torque when the mechanical device is twisted. The torsion spring will return to its original position when the twisting force is removed.

Trigger: As used in this disclosure, a trigger is a lever that operates in conjunction with a spring or similar device such that: 1) the lever is used to activate a mechanism; and 2) the spring or similar device returns the lever to its original position after the mechanism has been activated.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:
1. A calibrated measuring instrument comprising
a cap, a body, and a leveler;
wherein the cap and the leveler are attached to the body;
wherein the calibrated measuring instrument is measuring volume;
wherein the calibrated measuring instrument is configured for use with an analyte material;
wherein the analyte material refers to the material being measured within the calibrated measuring instrument;
wherein the calibrated measuring instrument is selected from the group consisting of: a fluid analyte material, a semi-rigid analyte material, a granular analyte material, or a crystalline analyte material;
wherein the body is a contained and calibrated volume that is used to measure the volume of the analyte material;
wherein the cap is used to manipulate the calibrated measuring instrument;
wherein the leveler is a device that levels the analyte material within the body of the calibrated measuring instrument;
wherein the cap is a structure that forms the superior end of the calibrated measuring instrument;
wherein the cap comprises a grip, a first lever, and a second lever;
wherein the first lever and the second lever are attached to the grip;
wherein the grip is further defined with a first end and a second end;
wherein the grip is a U shaped structure;
wherein the grip attaches to the superior end of the body.
2. The calibrated measuring instrument according to claim 1
wherein the first lever is a mechanical trigger that releases the measured analyte material from the body;
wherein the second lever is a mechanical trigger that rotates the leveler.
3. The calibrated measuring instrument according to claim 2
wherein the grip comprises a center chamber;

wherein the center chamber is a negative space that forms a continuous channel from the first end of the grip to the second end of the grip.

4. The calibrated measuring instrument according to claim 3
wherein the body comprises a cylinder and a cone;
wherein the cylinder is further defined with a cylinder center axis, a cylinder face, a superior cylinder end, and an inferior cylinder end;
wherein the cone is further defined with a cone base, a cone face, and a cone apex;
wherein the cone attaches to the inferior cylinder end;
wherein the cylinder face refers to the face of the geometric cylindrical structure that forms the cylinder;
wherein the superior cylinder end refers to the base of the geometric cylindrical structure that forms the cylinder that is proximal to the superior side of the calibrated measuring instrument;
wherein the inferior cylinder end refers to the base of the geometric cylindrical structure that forms the cylinder that is proximal to the inferior side of the calibrated measuring instrument;
wherein the cone base refers to the base of the geometric cone structure that forms the cone;
wherein the cone face refers to the face of the geometric cone structure that forms the cone;
wherein the cone apex refers to the apex of the geometric cone structure that forms the cone;
wherein the cone apex is rounded.

5. The calibrated measuring instrument according to claim 4
wherein the body further comprises a calibrating indicia;
wherein the calibrating indicia refers to a plurality of markings that are formed on the body;
wherein each calibrating indicia indicates a level;
wherein the level indicated by each calibrating indicia communicates the volume within the body.

6. The calibrated measuring instrument according to claim 5
wherein the cylinder is a hollow cylindrical structure formed from a transparent material;
wherein the cylinder comprises a leveler slot, a linkage, and a coaxial chamber;
wherein the leveler slot and the coaxial chamber are formed within the cylinder;
wherein the linkage is installed within the cylinder;
wherein the coaxial chamber is a negative space that is formed within a curved plate that forms the cylinder.

7. The calibrated measuring instrument according to claim 6
wherein the first end of the grip attaches to the superior cylinder end such that the center chamber is aligned with the coaxial chamber of the cylinder;
wherein the second end of the grip attaches to the superior cylinder end;
wherein the alignment of the center chamber and the coaxial chamber allows the linkage to pass from the center chamber into the coaxial chamber.

8. The calibrated measuring instrument according to claim 7 wherein the coaxial chamber is formed from a segment of a cylindrical space that is positioned in a coaxial manner around the cylinder center axis of the cylinder.

9. The calibrated measuring instrument according to claim 8
wherein the leveler is an oval shaped plate;
wherein the leveler is further defined with a thickness;
wherein the leveler is further defined with a major axis and a minor axis;
wherein the minor axis of the leveler is lesser than the diameter of the cylinder such that the leveler can be inserted through the leveler slot into the interior of the cylinder;
wherein the leveler is attached to the cylinder using a pivot.

10. The calibrated measuring instrument according to claim 9
wherein the leveler slot is a slot shaped aperture that is formed through the cylinder face of the cylinder;
wherein the inner dimension of the leveler slot is greater than the thickness of the outer dimension of the leveler such that the leveler can be inserted into the interior space of the cylinder through the leveler slot.

11. The calibrated measuring instrument according to claim 10
wherein the cone is a hollow cone shaped structure formed from a transparent material;
wherein the cone is divided into two partial cone structures by a plane that is parallel to the cone center axis;
wherein the cone comprises a first bifurcation, a second bifurcation, a first hinge, and a second hinge;
wherein the first hinge attaches the first bifurcation to the cylinder;
wherein the second hinge attaches the second bifurcation to the cylinder;
wherein the first bifurcation is a first partial cone structure selected from the two partial cone structures;
wherein the second bifurcation is a second partial cone structure selected from the two partial cone structures;
wherein the first bifurcation and the second bifurcation are identical;
wherein the first bifurcation and the second bifurcation are joined together to form the cone;
wherein the cone is further defined with an open position and a closed position;
wherein when the cone is in the open position, the analyte material will fall out of the body.

12. The calibrated measuring instrument according to claim 11
wherein the first hinge is a spring loaded hinge that attaches the first bifurcation to the inferior cylinder end of the cylinder;
wherein the first hinge attaches the first bifurcation to the inferior cylinder end of the cylinder;
wherein the second hinge is a spring loaded hinge;
wherein the second hinge attaches the second bifurcation to the inferior cylinder end of the cylinder;
wherein the first hinge and the second hinge are identical.

13. The calibrated measuring instrument according to claim 12
wherein the first hinge attaches the first bifurcation to the cylinder such that when the cone is in the open position the spring of the first hinge in in its relaxed shape;
wherein the second hinge attaches the second bifurcation to the cylinder such that when the cone is in the open position the spring of the second hinge in in its relaxed shape.

14. The calibrated measuring instrument according to claim 13
wherein the spring of the first hinge is held in the closed position using a first detent that connects through the linkage to the first lever such that the first lever will release the first detent holding the first hinge in the closed position;

wherein the second hinge is held in the closed position using a second detent that connects through the linkage to the first lever such that the first lever will release the second detent holding the second hinge in the closed position.

15. The calibrated measuring instrument according to claim 14 wherein the diameter of the cone base equals the diameter of the inferior cylinder end such that the cone base can be aligned and attached to the inferior cylinder end.

16. The calibrated measuring instrument according to claim 15
   wherein the linkage is a spring driven mechanical device that mechanically connects the first lever to the first hinge;
   wherein the linkage is a spring driven mechanical device that mechanically connects the first lever to the second hinge;
   wherein the linkage enables the first lever to release the first hinge;
   wherein the linkage enables the first lever to release the second hinge.

17. The calibrated measuring instrument according to claim 16 wherein the first bifurcation and the second bifurcation are manually held in the closed position while the first hinge and the second hinge and placed in their closed and locked positions.

18. The calibrated measuring instrument according to claim 17 wherein the first lever is activated to release the first hinge and the second hinge respectively thereby opening the body to release the analyte material.

\* \* \* \* \*